(12) United States Patent
Rackley

(10) Patent No.: US 9,017,303 B2
(45) Date of Patent: Apr. 28, 2015

(54) SELECTIVE-CAPACITY BODILY FLUIDS COLLECTION AND DRAINAGE DEVICE

(76) Inventor: J. Daniell Rackley, Tallahassee, FL (US)

(*) Notice: Subject to any disclaimer, the term of this patent is extended or adjusted under 35 U.S.C. 154(b) by 363 days.

(21) Appl. No.: 13/437,568

(22) Filed: Apr. 2, 2012

(65) Prior Publication Data

US 2013/0261573 A1    Oct. 3, 2013

(51) Int. Cl.
*A61F 5/44* (2006.01)
*A61M 25/00* (2006.01)
*A61F 5/48* (2006.01)
*A61M 39/22* (2006.01)
*A61M 1/00* (2006.01)

(52) U.S. Cl.
CPC ............... *A61F 5/44* (2013.01); *A61M 25/002* (2013.01); *A61F 5/4408* (2013.01); *A61F 5/48* (2013.01); *A61M 39/22* (2013.01); *A61F 5/4407* (2013.01); *A61F 2005/4402* (2013.01); *A61M 1/0021* (2013.01); *A61M 39/223* (2013.01); *A61F 5/4404* (2013.01); *A61M 25/0017* (2013.01); *A61F 5/4405* (2013.01)

(58) Field of Classification Search
CPC ....... A61F 5/44; A61F 5/4405; A61F 5/4404; A61F 5/4407; A61F 5/4408; A61F 5/48; A61F 2005/44; A61F 2005/4402; A61F 2005/445; A61M 25/0017; A61M 25/002; A61M 39/22; A61M 39/223; A61M 39/28; A61M 39/284; A61M 39/285; A61M 39/286; A61M 39/288; A61M 1/0021; A61J 1/05; A61J 1/10; A61J 1/14; A61J 1/1412; A61J 1/1462; A61J 1/1475; A61J 1/2093; A61B 5/20; A61B 5/208; A61B 5/4404; A61B 5/44; A61B 5/0085

See application file for complete search history.

(56) References Cited

U.S. PATENT DOCUMENTS

| | | | | |
|---|---|---|---|---|
| 3,187,750 | A | * | 6/1965 | Tenczar, Jr. .................... 604/410 |
| 3,554,256 | A | | 1/1971 | Andersen |
| 3,602,223 | A | * | 8/1971 | Engelsher ...................... 604/325 |
| 3,603,366 | A | | 9/1971 | Albizati |
| 3,650,272 | A | * | 3/1972 | Ericson ......................... 604/325 |
| 3,678,959 | A | * | 7/1972 | Liposky ................... 137/625.11 |

(Continued)

FOREIGN PATENT DOCUMENTS

DE       4034311 C1 *  1/1992  ............... A61G 9/00

OTHER PUBLICATIONS

Google Machine translation of DE4034311 C1. Wed Feb 18, 2015. https://www.google.com/patents/DE4034311C1.*

*Primary Examiner* — Adam Marcetich
(74) *Attorney, Agent, or Firm* — Adrienne C. Love

(57) ABSTRACT

A selective-capacity collection and drainage device having a first collection container, a second collection chamber and a common inlet valve characterized by a capacity selector and a common outlet valve connecting to each collection chamber. The common inlet valve consists of a common inflow tube, which connects via tubing to the catheter where bodily fluids will enter the selective capacity chamber. The inlet valve has a capacity-selector located between the common inflow tube and the multi-chambered container, such that bodily fluids are directed by the capacity-selector into one or all of the collection chambers via the divided inflow tube. Each individual chamber of the multi-chambered container is connected at its base to the common outlet valve. The common outlet valve consists of a divided outflow tube on top, which connects to each collection chamber, and converges at an outflow valve.

15 Claims, 14 Drawing Sheets

(56) References Cited

U.S. PATENT DOCUMENTS

| | | | |
|---|---|---|---|
| 3,943,929 A * | 3/1976 | Patel | 604/544 |
| 3,974,533 A * | 8/1976 | Klecker | 4/455 |
| 4,265,243 A * | 5/1981 | Taylor | 604/128 |
| 4,291,706 A * | 9/1981 | Voges et al. | 600/575 |
| 4,306,705 A * | 12/1981 | Svensson | 251/149.9 |
| 4,421,509 A | 12/1983 | Schneider | |
| 4,865,046 A * | 9/1989 | Duran | 600/575 |
| 4,938,747 A | 7/1990 | Wallace | |
| 4,955,879 A | 9/1990 | Mervine | |
| 5,509,898 A * | 4/1996 | Isono et al. | 604/87 |
| 7,487,888 B1 * | 2/2009 | Pierre, Jr. | 222/144.5 |
| 7,942,578 B2 | 5/2011 | Andersen | |
| 2007/0287966 A1 * | 12/2007 | Keeley | 604/246 |
| 2008/0091153 A1 | 4/2008 | Harvie | |
| 2008/0147025 A1 | 6/2008 | Van Gompel | |
| 2008/0172016 A1 * | 7/2008 | House | 604/317 |
| 2010/0286650 A1 * | 11/2010 | Fitzgerald | 604/500 |

\* cited by examiner

SELECTIVE-CAPACITY BODILY FLUIDS COLLECTION AND DRAINAGE DEVICE

CROSS-REFERENCES TO RELATED APPLICATIONS

Not Applicable

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of devices made for collection and drainage of bodily fluids, particularly urine. More specifically, the invention comprises two separate but adjoined collection chambers with a common outflow tube and a capacity selector that can be positioned to allow inflow of bodily fluids into one or both chambers, such that the device can be used for both smaller volume collection during ambulatory daytime use as well as for larger volume nighttime collection.

2. Description of the Related Art

When a person's natural ability to expel bodily fluids becomes impaired, such as with postoperative patients or those who have neurogenic bladders or benign prostatic enlargement, in many cases an artificial collection system is introduced to allow for artificial urinary drainage. This collection system consists of an indwelling tube, or "catheter", which is introduced into the bladder, and an external collection and drainage bag, which is connected via tubing to the catheter.

Users of this collection system often need to employ two different bag sizes: a smaller bag that can be strapped to the leg or waist to facilitate ambulatory activities, such as during the day; and a larger bag that is used for stationary collection while the user is sleeping, such as at night. The smaller bag is lighter and can be more easily hidden under clothing during the day. This accommodates the user's movements during the day, while remaining discretely concealed, reducing the stigma of this often times embarrassing situation. Using this same smaller bag at night, however, can be problematic as the bag quickly fills to capacity and the user's sleep must be repetitively interrupted so that the bag can be drained or the user risks infection from the overflow of urine itself, which can be colonized with bacteria. Therefore, users of this collection system generally change to a larger bag at night, which can be placed at the bedside and can hold a larger amount of fluids.

Unfortunately, utilizing the present arrangement of two different bags requires the user to open the collection system in order to change bags at least once a day. Significantly, each time the system is opened, the user is exposed to a high risk of infection. Moreover, urine continues to flow from the catheter when a bag is disconnected, which can easily result in the soiling of the user's clothing or restroom. Additionally, for elderly users, or those with other physical or cognitive impairments, the physical task of changing bags can be difficult or even painful.

Furthermore, there is no way to accomplish a change of bags discretely or in an impromptu situation, such as when the user is in public, or is in an unexpectedly prolonged business meeting, and finds him or herself with a filled smaller bag but without the means or time to get to a bathroom to empty it. Even utilizing a larger bag during the day to avoid such an embarrassing situation is impractical and problematic in and of itself.

First, if the larger bag is only being employed as a day bag, the excess portion must be folded up and behind the top portion. This can lead to embarrassing bulges when gravity or pressure causes fluid to seep up under the fold into the back portion of the bag. Moreover, as the bottom of the bag bulges, pressure on the straps holding the bag to the leg or waist of the user will increase, which can lead to decreased circulation in the user's leg or waist.

Second, once in the folded position, the bag cannot be unfolded to allow for more comfortable and discreet containment unless the user first disrobes, unstraps the bag from his or her body, and then unfolds the bag. Thus, there is no discrete way to achieve larger containment capacity from the folded position in an emergency situation.

In order to significantly reduce the risk of infection, eliminate the embarrassing and unsanitary risk of urine overflow, and provide users with a means by which to protect themselves from embarrassment in an emergency situation, a device is needed that eliminates the need to change bags but that retains the discretion and comfort of a smaller bag during the day while still being able to hold a larger volume of fluid in the event of an unexpected social situation or regularly during the night. The present invention achieves this objective, as well as others, as explained in the description below.

BRIEF SUMMARY OF THE INVENTION

A selective-capacity bodily fluids collection and drainage device is shown and described. The selective-capacity collection and drainage device is generally comprised of a multi-chambered collection container, a common inlet valve characterized by a capacity selector, and a common outlet valve connecting to each collection chamber.

The multi-chambered collection container is formed of a flexible liquid-impermeable material, such as plastic, such that each individual collection chamber can be folded along the seam connecting it to the adjacent chamber when not in use. Each chamber will lay flat when not in use and can be secured in a folded position with a strip of interlocking material, such as hook and loop, corresponding to another strip such material on the back of the collection container.

The common inlet valve consists of a common inflow tube, which connects via tubing to the catheter where bodily fluids, such as urine, will enter the selective capacity chamber. The inlet valve is characterized by a capacity-selector located below the common inflow tube. The capacity-selector can be positioned to allow bodily fluids to flow into one or all of the collection chambers via the divided inflow tube based on the collection capacity needed by the user. The capacity selector will allow the user to engage only one collection chamber, such as during more ambulatory daytime use, or to engage multiple collection chambers simultaneously, such as during nighttime use, without requiring the user to change from a smaller to larger bag. Furthermore, when the multi-chambered collection container remains in an unfolded position, the capacity selector will allow the user to switch from single-chambered use to multi-chambered use without having to adjust the collection chambers or remove or reposition the device, such as when the user unexpectedly finds that he or she is unable to empty a full single chamber.

Each individual chamber of the multi-chambered container is connected at its base to the common outlet valve. The common outlet valve consists of a divided outflow tube on top, which connects to each collection chamber, and converges at an outflow valve that allows or prevents fluid flowing out of the collection chambers, through the common outflow tube and into a disposal container, such as the toilet.

Figure 1:
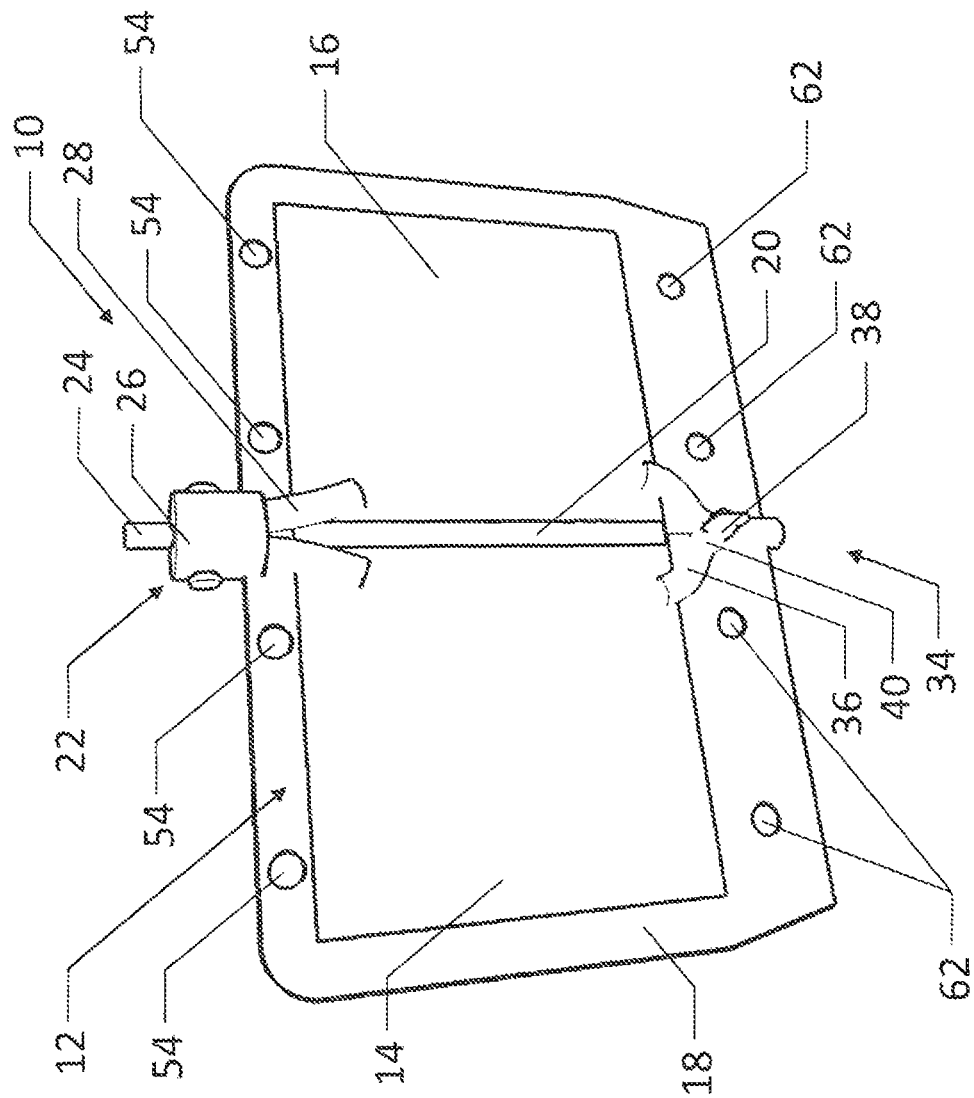
FIG. 1 is a perspective view, showing the preferred embodiment of the present invention.

| REFERENCE NUMERALS IN THE DRAWINGS | | | |
|---|---|---|---|
| 10 | collection and drainage device | 12 | multi-chambered collection container |
| 14 | first collection chamber | 16 | second collection chamber |
| 18 | outer casing | 20 | seam |
| 22 | common inlet chamber | 24 | common inflow tube |
| 26 | capacity selector | 28 | divided inflow tube |
| 30 | first inflow tube prong | 32 | second inflow tube prong |
| 34 | common outlet chamber | 36 | divided outflow tube |
| 38 | common outflow valve | 40 | common outflow tube |
| 42 | catheter tube | 44 | upper tube prong opening |
| 46 | lower anti-reflux flap | 50 | internal valve control member |
| 52 | external valve control member | 54 | top strap holes |
| 56 | working spool | 58 | stem |
| 60 | overflow valve | 62 | bottom strap holes |
| 70 | first interlocking side member | 72 | second interlocking side member |
| 74 | opening to common inflow tube | 76 | control valve |
| 78 | directional arrow | 82 | interlocking seam |
| 84 | first interlocking seam side member | 86 | second interlocking seam side member |
| 90 | internal outflow opening | 92 | external outflow tube opening |
| 94 | directional arrow | 96 | directional arrow |
| 98 | directional arrow | 100 | user's leg |
| 102 | strap | 104 | top of outer casing |
| 106 | side of outer casing | 108 | side of outer casing |
| 110 | bottom of outer casing | 112 | capacity selector chamber |
| 114 | zipper | | |

DETAILED DESCRIPTION OF THE INVENTION

FIG. 1 illustrates the present invention in the preferred embodiment. The collection and drainage device 10 is generally made up of multi-chambered collection container 12, common inlet chamber 22, and common outlet chamber 34. Multi-chambered collection container 12, common inlet chamber 22, and common outlet chamber 34 are housed in outer casing 18.

Figure 10:
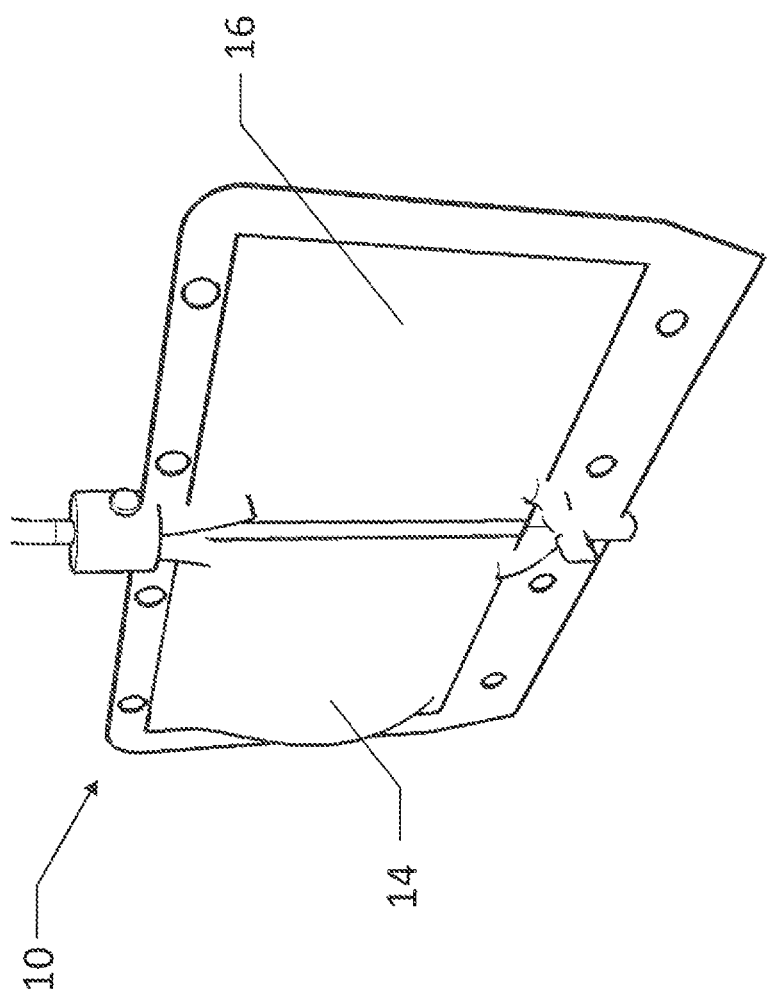
FIG. 10 is a perspective view, showing the preferred embodiment of the present invention from the back with only one collection chamber being filled.
Figure 11:
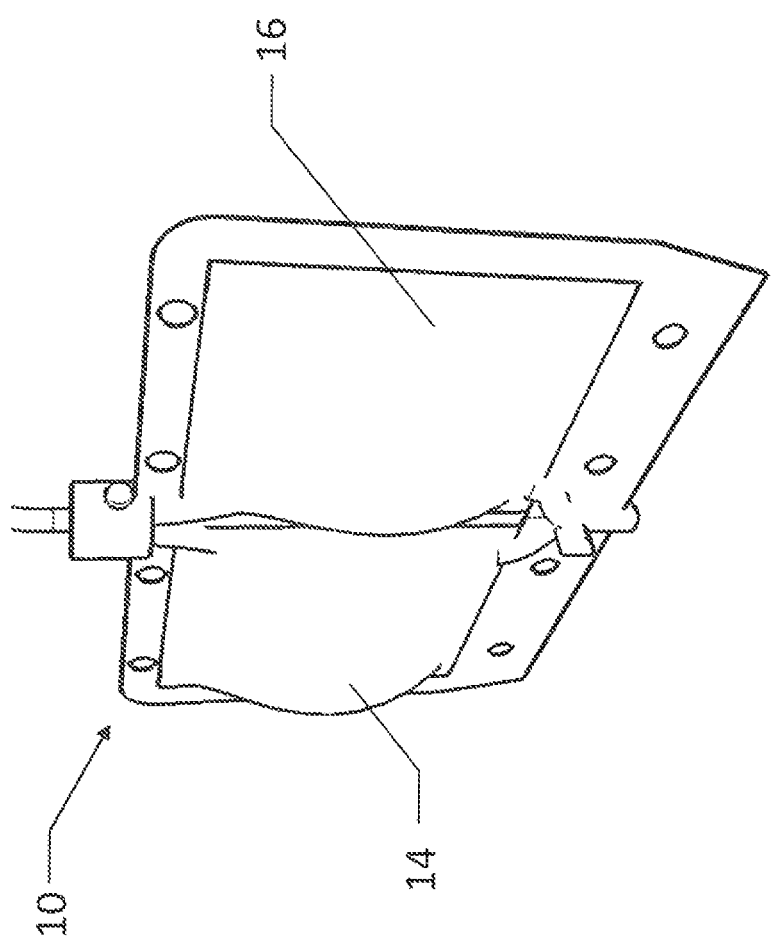
FIG. 11 is a perspective view, showing the preferred embodiment of the present invention from the back with both collection chambers being filled.

Multi-chambered collection container 12 generally comprises two collection chambers, first collection chamber 14 and second collection chamber 16, in the preferred embodiment. However, multi-chambered collection container 12 can comprise more than two collection chambers. First collection chamber 14 and second collection chamber 16 can be made up of any flexible material that is impervious to bodily fluids, such as plastic, and is capable of lying flat when empty, as shown in FIG. 1, and expanding when filled, as shown in FIG. 10 and FIG. 11. Returning to FIG. 1, first collection chamber 14 and second collection chamber 16 are housed in outer casing 18 and abut at seam 20 of outer casing 18.

Figure 8:
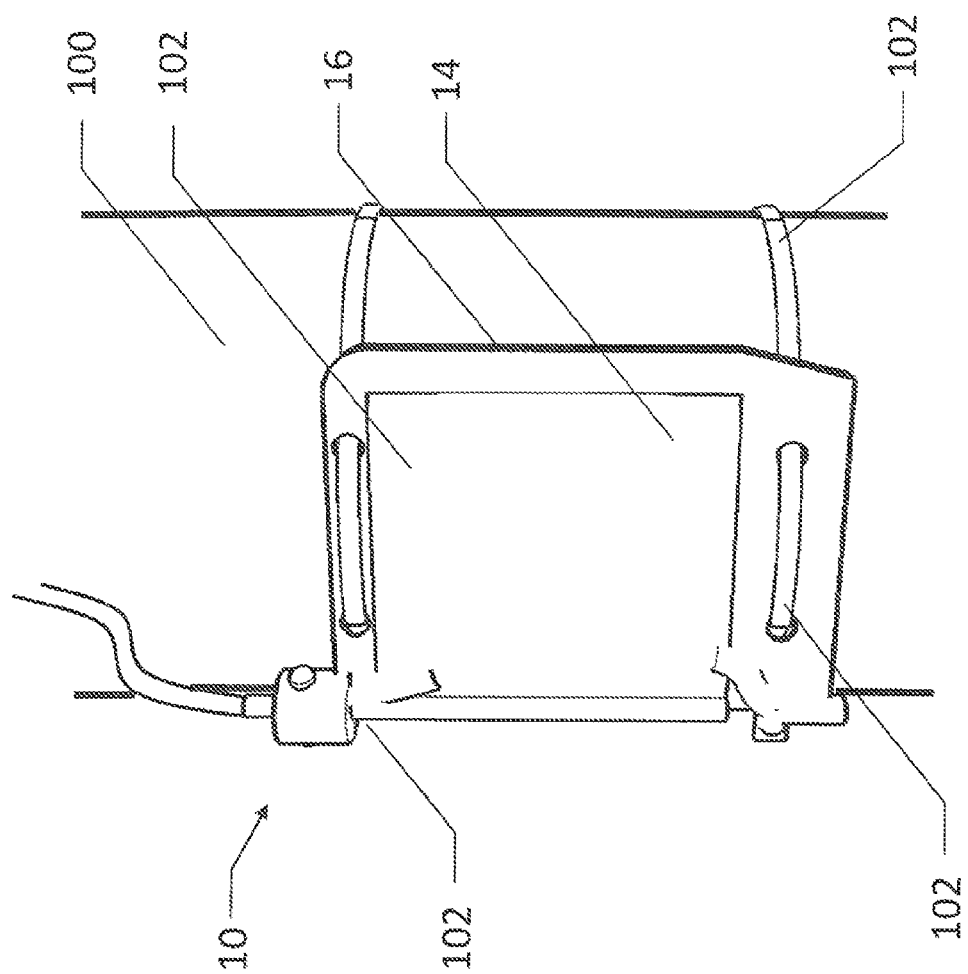
FIG. 8 is a perspective view, showing the preferred embodiment of the present invention being worn by a user when only the first collection chamber has been selected to fill.

Outer casing 18 can be made of any smooth, flexible material, such as plastic. In the preferred embodiment, there are four top strap holes 54 in the top of outer casing 104, and four bottom strap holes 62 in the bottom of outer casing 110. In the preferred embodiment, shown in FIG. 1, the strap holes on the top and bottom are positioned so that when collection and drainage device 10 is in the folded position, as shown in FIG. 8, the strap holes align. However, there can be more than four strap holes in each of the top and bottom of outer casing 104 and 110 such that they align when folded as illustrated in FIG. 8.

Figure 7:
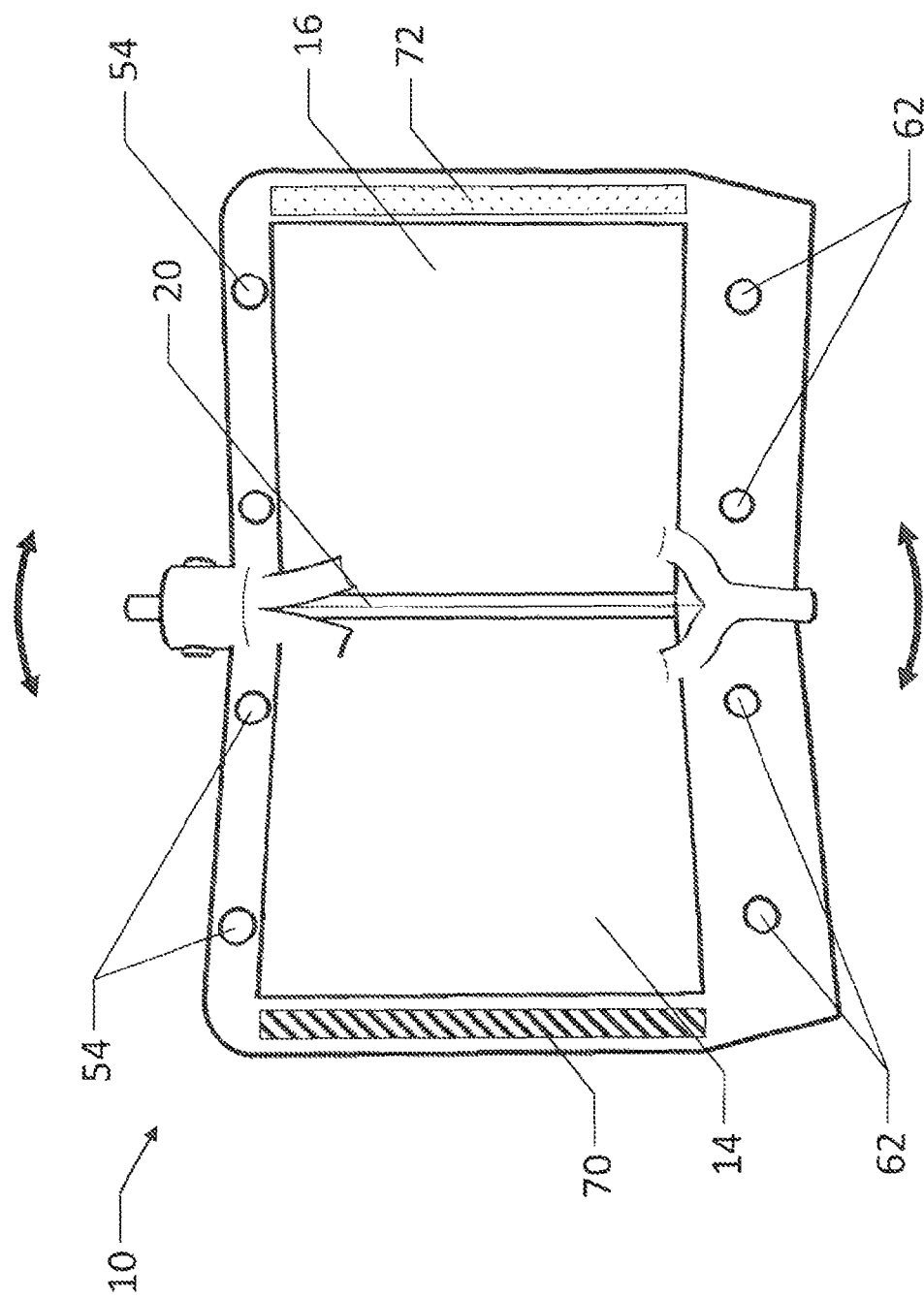
FIG. 7 is a perspective view, showing the back of the present invention in a partially folded position.

FIG. 7 is a perspective view of collection and drainage device 10 as shown from behind. As shown in FIG. 7, collection and drainage device 10 can be folded along seam 20, as indicated by the directional arrows, when only one collection chamber is in use. In the preferred embodiment of the present invention, along each side of outer casing 106 and 108 there are strips of interlocking side members—first interlocking side member 70 and second interlocking side member 72—that fasten the sides of outer casing 106 and 108 together when in the folded position. Interlocking side members 70 and 72 can be made of any light strips of interlocking material, such as a hook and loop system like Velcro®, a registered trademark, or a groove and ridge system, like Ziploc®, a registered trademark, or even opposed pairs of interlocking discs, such as snap fasteners.

Figure 2:
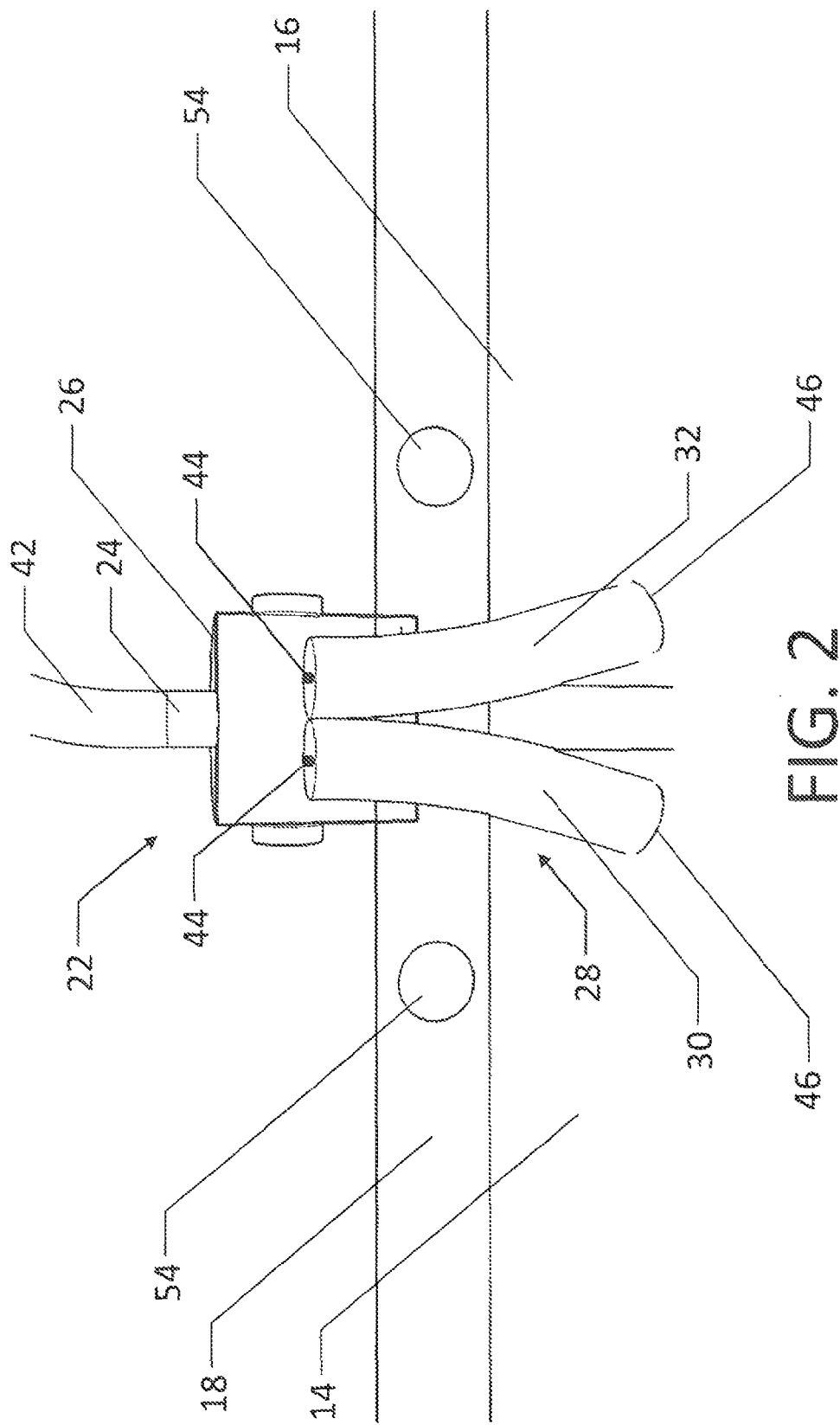
FIG. 2 is a perspective view, showing the preferred embodiment of the common inlet chamber of the present invention.

Returning to FIG. 1, common inlet chamber 22 comprises common inflow tube 24, capacity selector 26, and divided inflow tube 28. As shown in FIG. 2, catheter tube 42 connects common inflow tube 24 to the user's catheter. Common inflow tube 24 also connects to capacity selector 26, which connects to a divided inflow tube 28.

As shown in FIG. 2, divided inflow tube 28 comprises first inflow tube prong 30 and second inflow tube prong 32, which extend up into capacity selector 26. In the preferred embodiment, both the first inflow tube prong 30 and the second inflow tube prong 32 have an upper tube prong opening 44, which open into capacity selector 26, and a lower anti-reflux flap 46. The lower anti-reflux flap 46 can be formed of any type of one-way valve that is capable of preventing bodily fluids from flowing back up into the catheter. The lower anti-reflux flaps 46 of both first inflow tube prong 30 and second inflow tube prong 32 open into first collection chamber 14 and second collection chamber 16 respectively.

Figure 3:
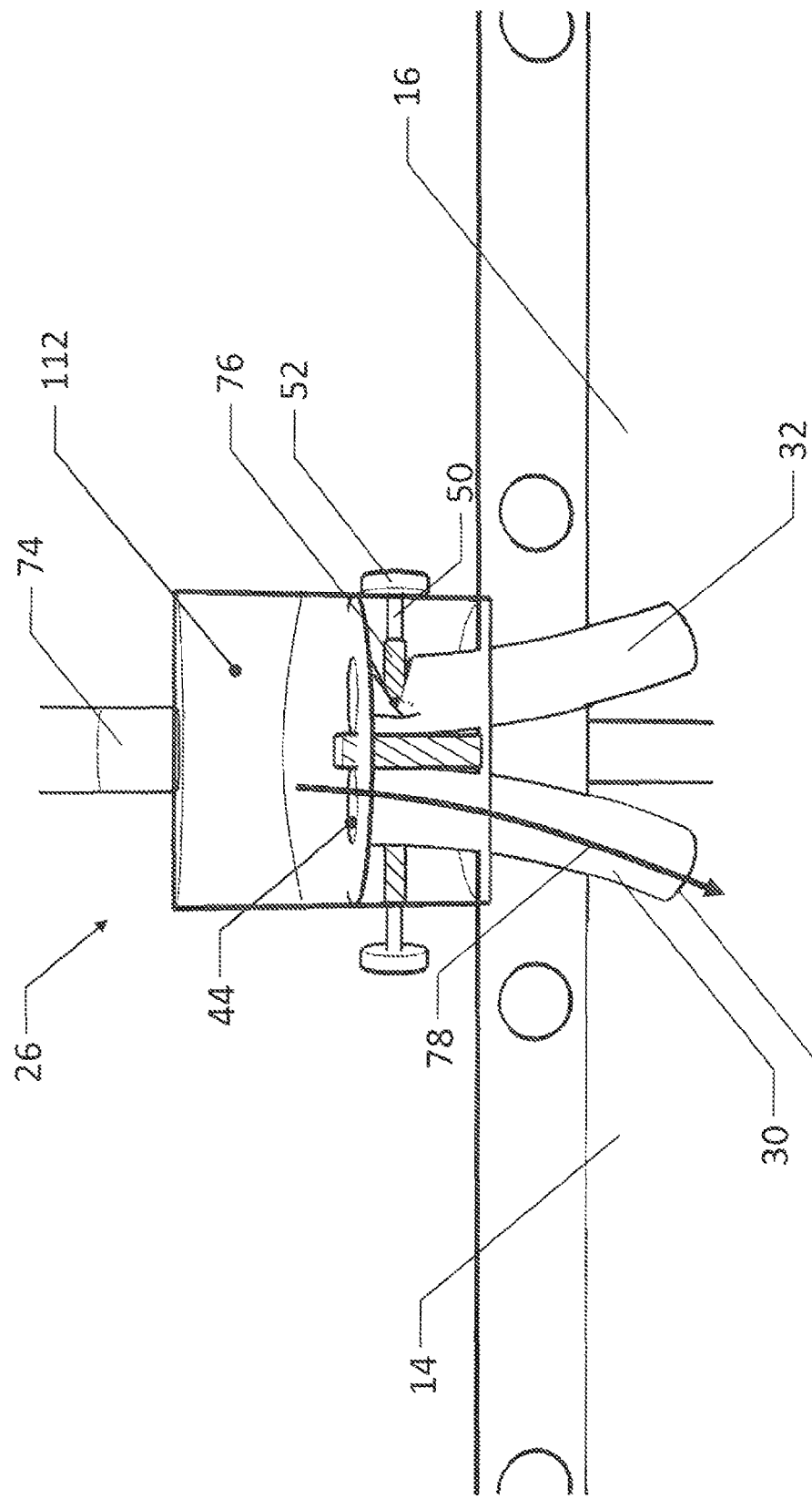
FIG. 3 is a cut-away view of the capacity selector, showing the control valve.
Figure 4:
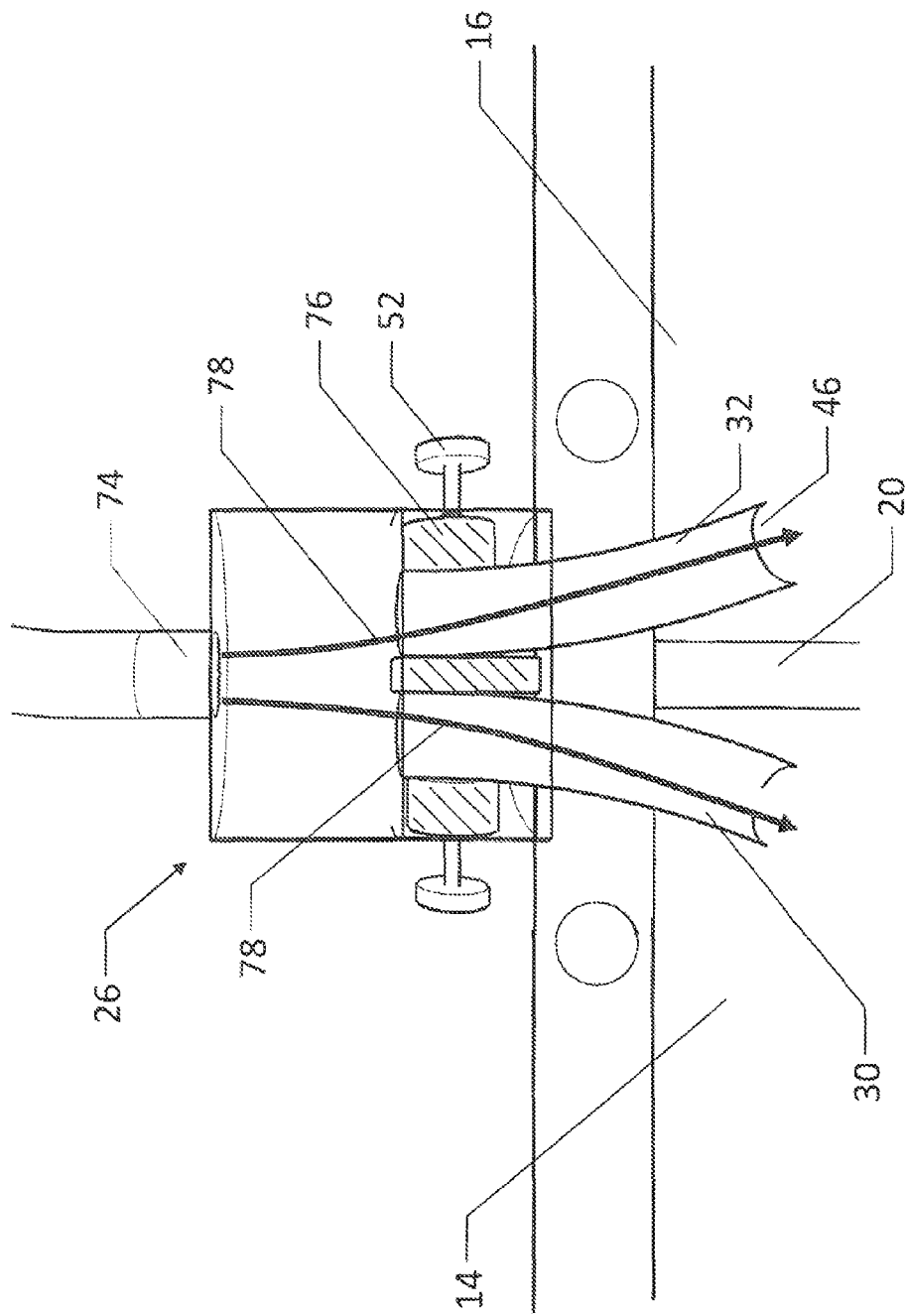
FIG. 4 is a cut-away view of the capacity selector, showing the control valve positioned to allow flow through the first inflow tube prong.

FIG. 3 shows a detailed cut-away view of capacity selector 26. Capacity selector 26 is comprised of at least one control valve 76, which has an open position and a closed position (see FIG. 3 showing valve 76 in the closed position over second inflow tube prong 32; and FIG. 4 showing valve 76 in the open position, allowing flow of bodily fluids through first and second inflow tube prongs 30, 32). As illustrated in FIG. 3, external valve control member 52 allows the user to control whether the control valve is in an open position or a closed position.

Control valve 76 can be formed by any type of valve system including a multi-way directional control valve, such as a three-way ball valve, a three-way stopcock, or a three-way spool valve, such as are used in hydraulics systems. In the preferred embodiment, control valve 76 controls the flow of bodily fluid through divided inflow tube 28, by blocking flow from or permitting flow through upper tube-prong opening 44 of first inflow tube prong 30 and second inflow tube prong 32. Internal valve control member 50 controls the positioning of control valve 76. Preferably, the user can adjust control valve 76 to achieve the desired capacity by positioning external valve control member 52 to the desired setting.

As shown in FIG. 3, when a user positions external valve control member 52 to allow flow through only first collection chamber 14, bodily fluid, as indicated by directional arrow 78, will enter into capacity selector 26 via opening to common inflow tube 74, flow through upper tube-prong opening 44 of first inflow tube prong 30 and out into first collection chamber 14 via lower anti-reflux flap 46. Lower anti-reflux flap 46 will prevent bodily fluid from flowing back up into the catheter, thus reducing the risk of infection to the user. In this configuration, control valve 76 will prevent fluid from entering into second inflow tube prong 32 and thus second collection chamber 16 will remain empty. Similarly, external valve control member 52 could also be positioned to allow flow through only second collection chamber 16, and first collection chamber 14 would remain empty.

FIG. 4 is a perspective view showing the flow of bodily fluid, indicated by directional arrow 78 through capacity selector 26 and into first collection chamber 14 and second collection chamber 16 when external valve control member 52 is positioned to a setting permitting flow through both first inflow tube prong 30 and second inflow tube prong 32 simultaneously.

Figure 5:
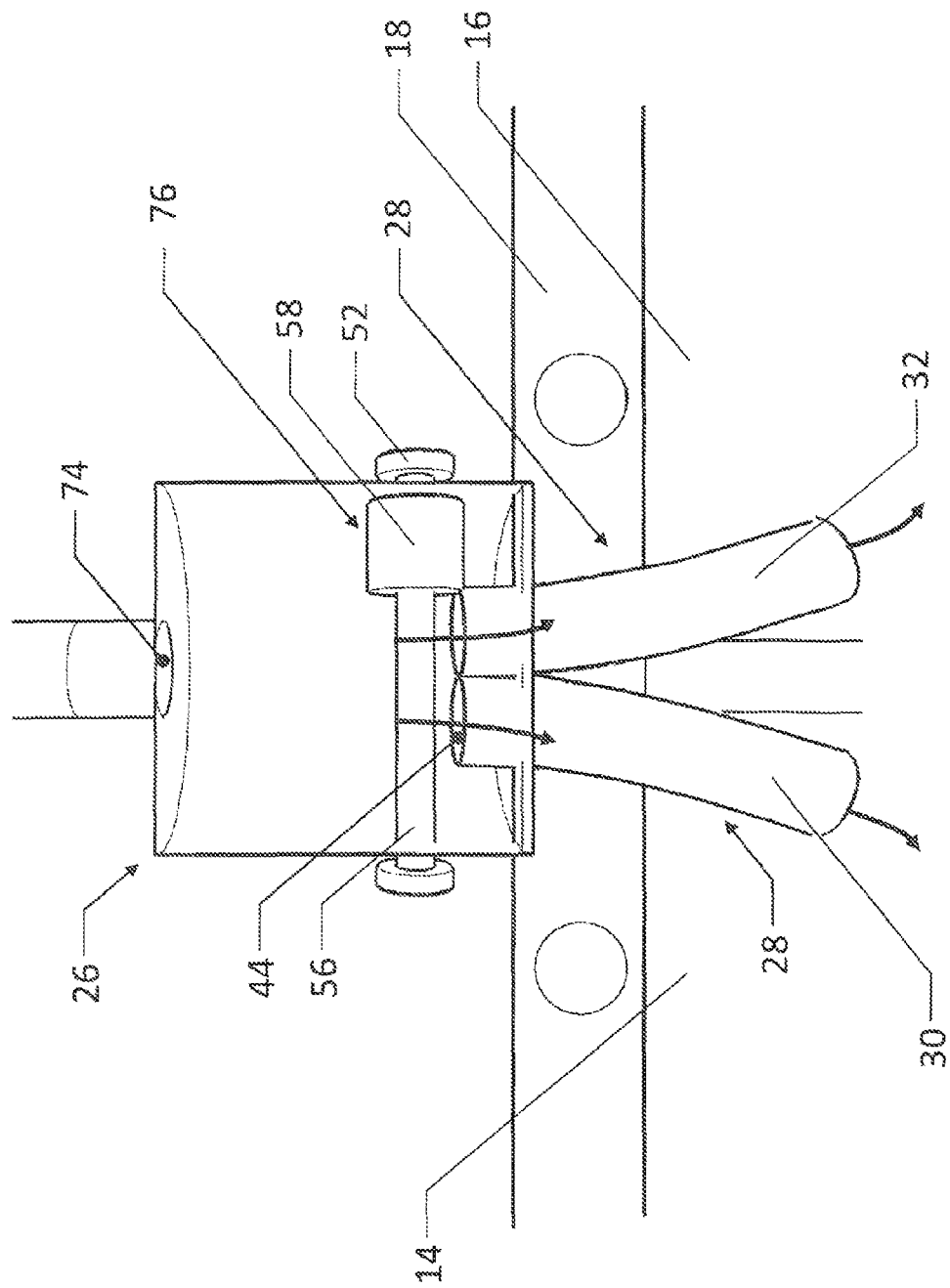
FIG. 5 is a cut-away view of the capacity selector in an alternate embodiment.

An alternate embodiment of the capacity selector 26 is illustrated in FIG. 5. Control valve 76 is comprised of working spool 56, external valve control member 52 and divided inflow tubes 28. The user selects the flow of bodily fluids by operating external valve control member 52 such that stem 58 shifts over divided inflow tubes 28, specifically upper tube-prong opening 44. In the open position, stem 58 sits by the side of upper tube prong opening 44 such that the flow of bodily fluid is directed through both first inflow tube prong 30 and second inflow tube prong 32. In the closed position (not shown), stem 58 sits over second inflow tube prong 32 preventing flow of bodily fluids into second collection chamber 16, thus directing flow solely into first collection chamber 14.

Returning to FIG. 1, fluid can be emptied from both first collection chamber 14 and second collection chamber 16 through common outlet chamber 34. Common outlet chamber 34 comprises divided outflow tube 36, outflow valve 38, and common outflow tube 40.

Figure 6:
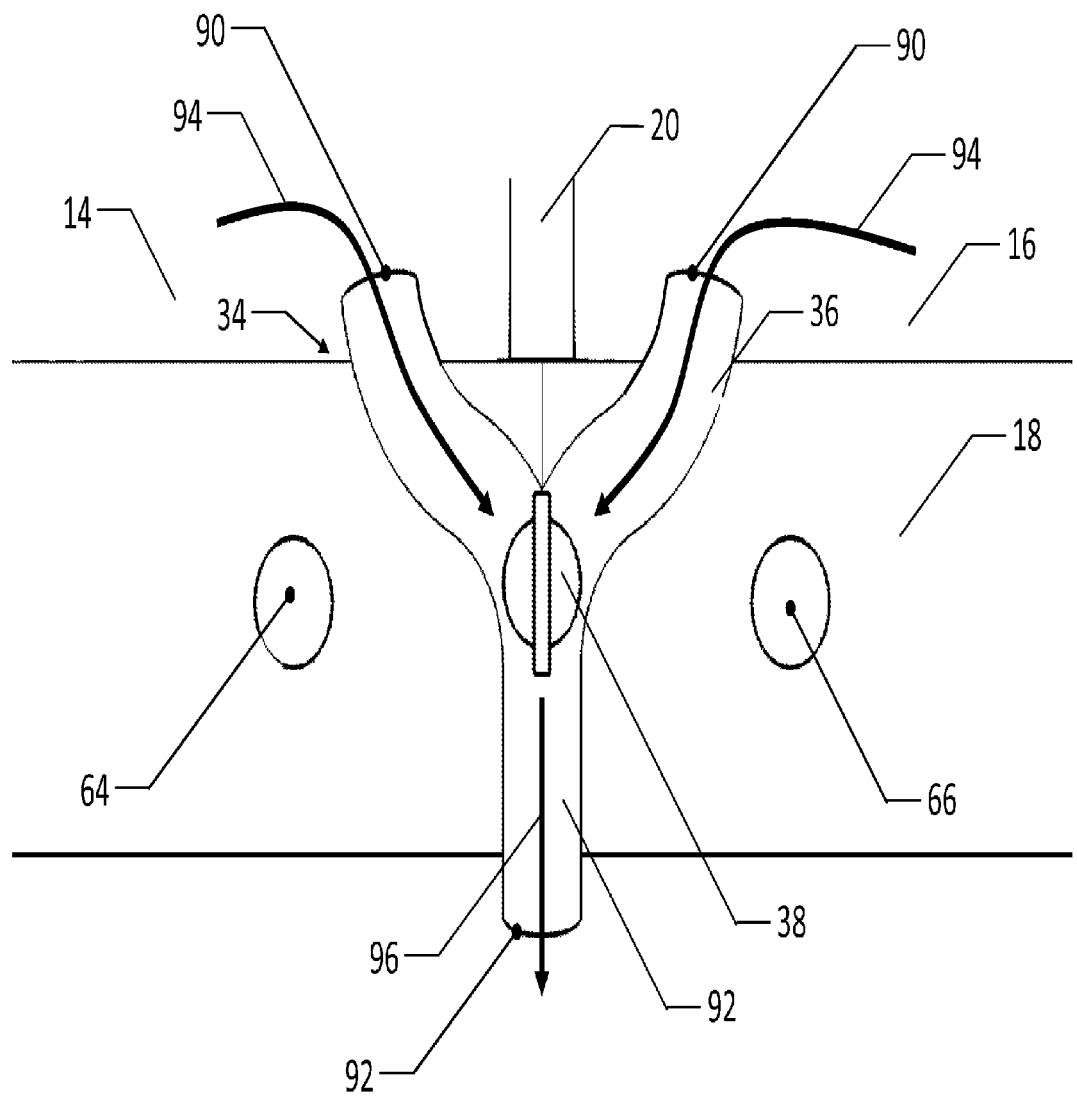
FIG. 6 is a perspective view, showing the preferred embodiment of the common outlet chamber of the present invention.

FIG. 6 is a perspective view of common outlet chamber 34 showing the flow of fluid, as indicated by directional arrows 94 and 96, as it is emptied out of first collection chamber 14 and second collection chamber 16. When the collection and drainage device 10 becomes full, a user can empty the fluid out into a disposal receptacle, such as a toilet, by opening common outflow valve 38. Common outflow valve 38 can be formed of any one-way valve, such as a fate valve, or stopcock valve. When common outflow valve 38 is open, fluid can flow out of first collection chamber 14 and second collection chamber 16 and into divided outflow tube 36 via the internal outflow tube openings 90, as indicated by directional arrows 94. The fluid will then pass through the open common outflow valve 38 and into common outflow tube 40. Once in common outflow tube 40, fluid can pass out through external outflow tube opening 92 and into a disposal receptacle, as indicated by directional arrow 96.

FIG. 8 is a perspective view of the present invention showing the preferred embodiment of collection and drainage device 10, as it might be worn in the folded position by a user when only first collection chamber 14 has been selected to be filled. As shown in FIG. 8, in the folded position, second collection chamber 16 is folded behind first collection chamber 14. Straps 102 secure collection and drainage device 10 to user's leg 100.

Figure 9:
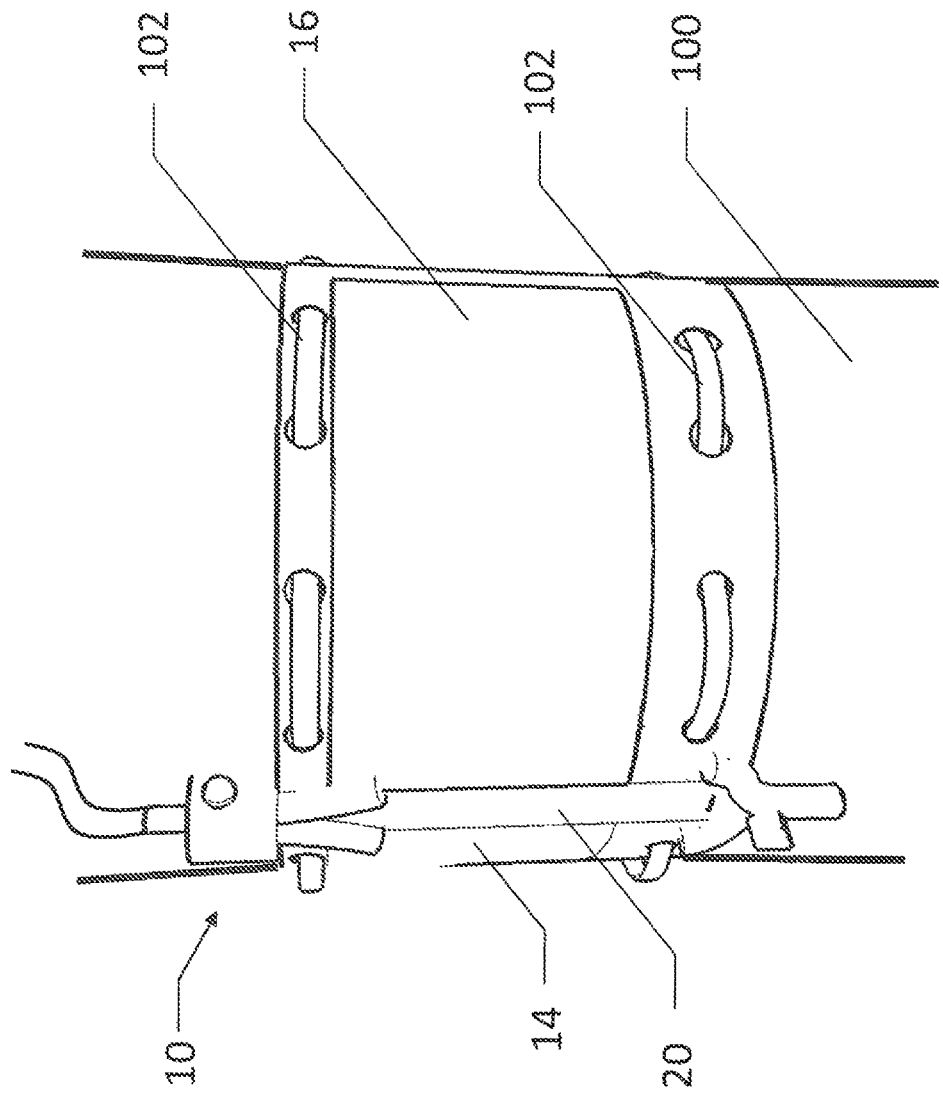
FIG. 9 is a perspective view, showing the preferred embodiment of the present invention being worn by a user when both collection chambers have been selected to fill.

FIG. 9 is a perspective view of the present invention showing the preferred embodiment of collection and drainage device 10 as it might be worn by a user when both first collection chamber 14 and second collection chamber 16 have been selected to be filled. As shown in FIG. 9, in the unfolded position, straps 102 secure collection and drainage device 10 to user's leg 100 permitting both first collection chamber 14 and second collection chamber 16 to fill at the same time.

FIG. 10 is a perspective view of the present invention from the back in an open position showing how first collection chamber 14 would expand when filled. In this view, only first collection chamber 14 has been selected to be filled.

FIG. 11 is a perspective view of the present invention from the back in an open position showing how first collection chamber 14 and second collection chamber 16 would expand when filled. In this view, both first collection chamber 14 and second collection chamber 16 have been selected to be filled.

Figure 12:
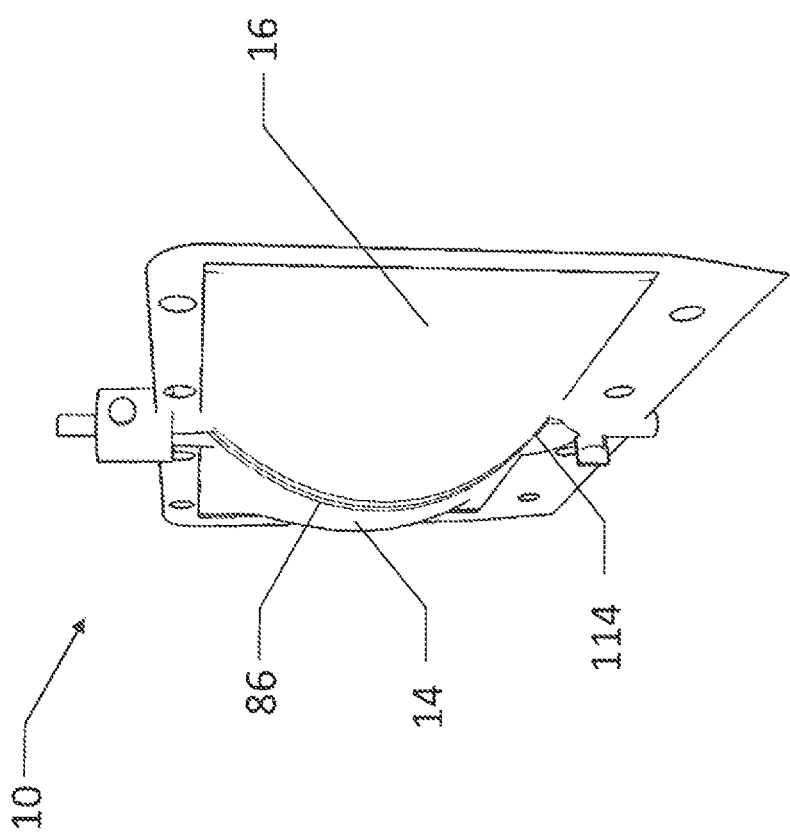
FIG. 12 is a perspective view, showing an alternative embodiment of the present invention.

FIG. 12 is a perspective view of collection and drainage device 10 in an alternative embodiment. In this alternative embodiment, first collection chamber 14 and second collection chamber 16 can be connected to allow fluid to pass freely between them at interlocking seam 86. Interlocking seam 86 is comprised of first interlocking seam side member 82, second interlocking seam side member 84, and zipper 114. Interlocking seam 86 can be formed of any groove and ridge system capable of creating a liquid-tight seal, such as Ziploc®, a registered trademark. In this view, interlocking seam 86 is in a closed position, separating first collection chamber 14 from second collection chamber 16.

Figure 13:
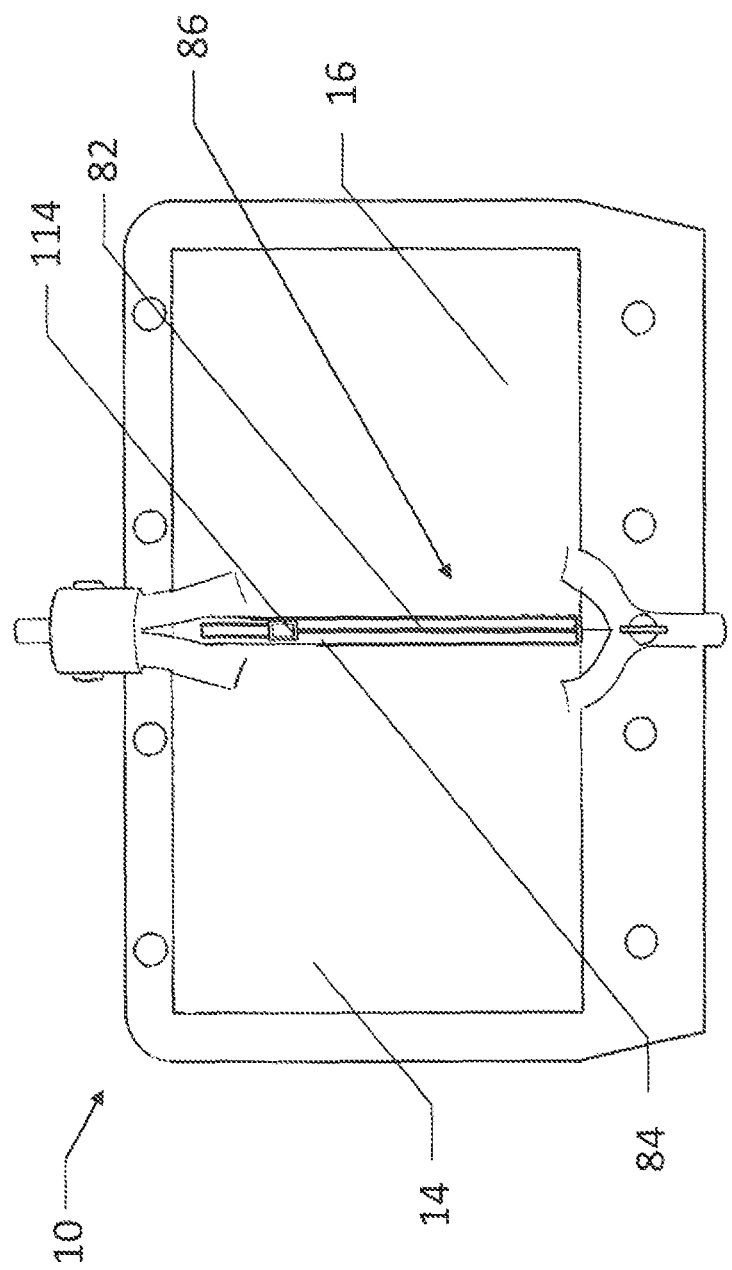
FIG. 13 is a perspective view, showing an alternative embodiment of the present invention with both chambers being filled.

When zipper 114 is positioned to separate first interlocking seam side member 82 from second interlocking seam side member 84, interlocking seam 86 is in an open position, as shown in FIG. 13. In this position, first collection chamber 14 and second collection chamber 16 are now fluidly connected by means of the open passageway created by the opened interlocking seam side members 84 and 86 and can expand simultaneously as if one large collection chamber.

Figure 14:
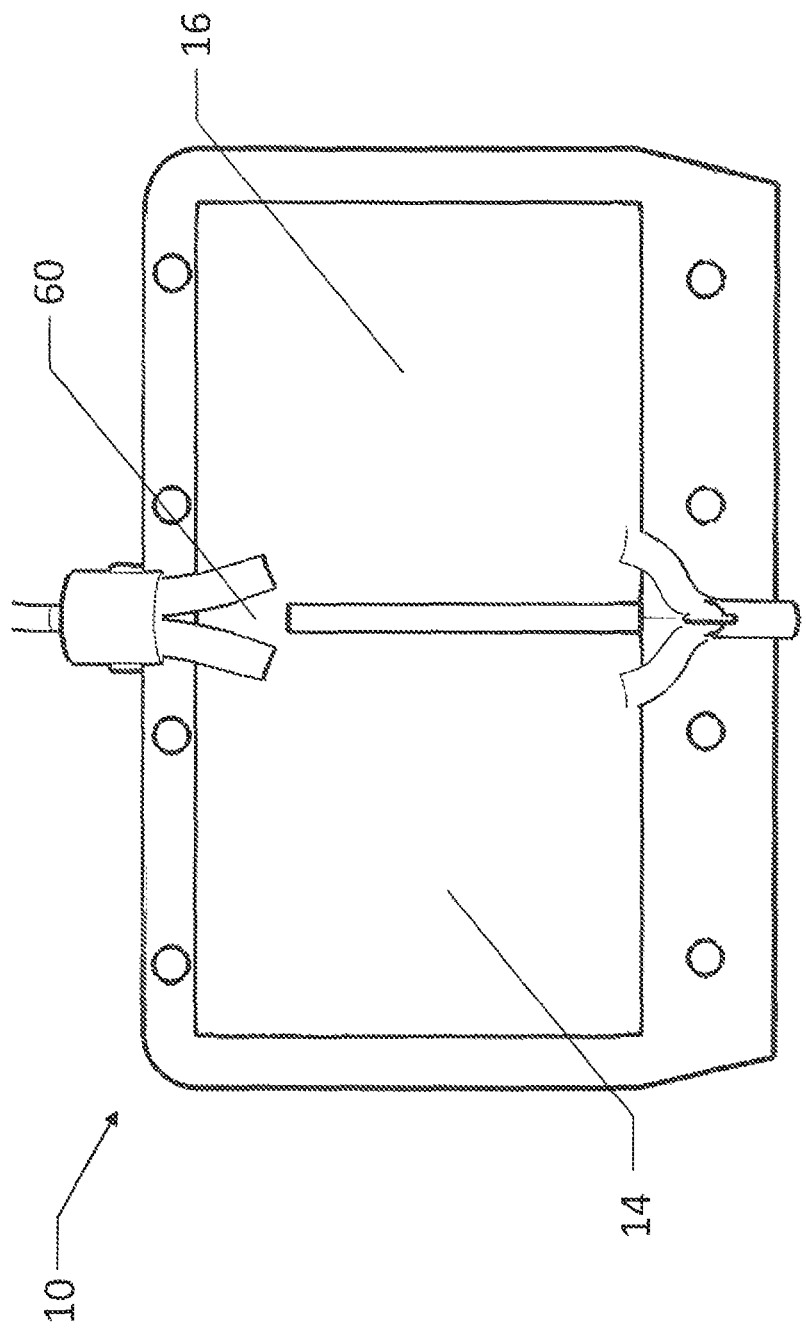
FIG. 14 is a perspective view, showing an optional overflow valve.

FIG. 14 illustrates another optional feature of the present collection and drainage device 10. At the top of first collection chamber 14 and second collection chamber 16 is an optional overflow valve 60 which can be added in order to prevent fluid backup in a situation in which the user fails to select both collection chambers but completely fills up the selected chamber. If that were to occur, overflow valve 60 would permit passage of fluid from a full first collection chamber 14 into second collection chamber 16.

The preceding description contains significant detail regarding the novel aspects of the present invention. It should not be construed, however, as limiting the scope of the invention but rather as providing illustrations of the preferred embodiments of the invention. As an example, divided inflow tube 28 could be formed of two separate tubes, multi-chambered collection container 12 could comprise three separate collection chambers, and first collection chamber 14 could be vertically adjacent to second collection chamber 16. Thus, the scope of the invention should be fixed by the following claims, rather than by the examples given above.

The invention claimed is:

1. A collection and drainage device to attach to a catheter by way of a catheter tube, for use by a user in collecting and draining bodily fluids and directing a flow of said bodily fluids, said collection and drainage device comprising:
   a. a multi-chambered collection container having a first collection chamber and a second collection chamber;
   b. a common inlet chamber for said bodily fluids further comprising:
      i. a common inflow tube for attachment to said catheter tube;
      ii. a divided inflow tube, fluidly attached to said common inflow tube, having a first inflow tube prong and a second inflow tube prong;
      iii a capacity selector, proximate said divided inflow tube such that said capacity selector can direct said flow of said bodily fluids into said multi-chambered collection container:
   c. a common outlet chamber for bodily fluids having:
      i. a first internal outflow tube opening and a second internal outflow tube opening;
      ii. a common outflow tube for said bodily fluids:
      iii. a common outflow valve such that said user can release said bodily fluid from said multi-chambered collection container;
   d. an outer casing having an outer portion and a vertical seam;
   e. wherein said multi-chambered collection chamber can be folded along said seam such that said first collection chamber is capable of being positioned behind said second collection chamber; and
   f. wherein said vertical seam fluidly separates said first collection chamber from said second collection chamber.

2. A collection and drainage device as recited in claim 1, wherein said capacity selector further comprises:
   a. at least one control valve proximate said second inflow tube prong having an open position and a closed position; and
   b. wherein in said closed position of said control valve, said bodily fluids are prevented from reaching said second collection chamber.

3. A collection and drainage device as recited in claim 1, wherein said capacity selector further comprises an external valve control member such that said user can select said open position of said valve or said closed position of said valve.

4. A collection and drainage device as recited in claim 1, wherein said capacity selector further comprises:
   a. a control valve comprised of a working spool positioned between said common inflow tube and said divided inflow tube, having a stem; and
   b. an external valve control member attached to said working spool such that said user can manipulate said working spool such that said stem blocks said flow of said bodily fluids from entering said second collection chamber.

5. A collection and drainage device as recited in claim 1, wherein said first inflow tube prong and second inflow tube prong further comprises:
   a. a first anti-reflux flap such that said first anti-reflux flap prevents said flow of said bodily fluid from flowing back into said catheter tube from said first collection chamber; and
   b. a second anti-reflux flap such that said second anti-reflux flap prevents said flow of said bodily fluid from flowing back into said catheter tube from said second collection chamber.

6. A collection and drainage device to attach to a catheter by way of a catheter tube, for use by a user in collecting and draining bodily fluids and directing a flow of said bodily fluids, said collection and drainage device comprising:

a. a common inlet chamber for said bodily fluids fluidly connected to said catheter tube;
b. wherein said common inlet chamber further comprises:
　i. a common inflow tube for attachment to said catheter tube;
　ii. a divided inflow tube, fluidly attached to said common inflow tube, having a first inflow tube prong and a second inflow tube prong;
　iii a capacity selector, proximate said divided inflow tube such that said capacity selector can direct said flow of said bodily fluids into said first inflow tube prong and said second inflow tube prong;
c. a first collection chamber fluidly connected to said common inlet chamber by way of said first inflow tube prong;
d. a second collection chamber fluidly connected to said common inlet chamber by way of said second inflow tube prong;
e. a common outlet chamber for bodily fluids having:
　i. a common outflow tube for said bodily fluids; and
　ii. a common outflow valve such that said user can release said bodily fluid from said first collection chamber and said second collection chamber,
f. wherein said multi-chambered collection chamber can be folded such that said first collection chamber is capable of being positioned behind said second collection chamber; and
g. wherein said first collection chamber is fluidly separate from said second collection chamber.

7. A collection and drainage device as recited in claim 6, further comprising an outer casing having an outer portion and a seam.

8. A collection and drainage device as recited in claim 7, further comprising a first interlocking side member proximate to said first collection chamber and a second interlocking side member attached proximate to said second collection chamber.

9. A collection and drainage device as recited in claim 7, wherein said multi-chambered collection chamber can be folded along said seam, wherein said first collection chamber is positioned behind said second collection chamber.

10. A collection and drainage device as recited in claim 9, wherein said multi-chambered collection chamber can be folded along said seam and said first collection chamber is capable of being positioned behind said second collection chamber such that said first interlocking side member and said second interlocking side member meet and temporarily affix to one another to hold said first collection chamber in place positioned behind said second collection chamber.

11. A collection and drainage device as recited in claim 7, further comprising an overflow valve fluidly connecting said first collection chamber to said second collection chamber.

12. A collection and drainage device as recited in claim 6, wherein said capacity selector further comprises:
　a. at least one control valve proximate said second inflow tube prong having an open position and a closed position; and
　b. wherein in said closed position of said control valve, said bodily fluids are prevented from reaching said second collection chamber.

13. A collection and drainage device as recited in claim 6, wherein said capacity selector further comprises an external valve control member such that said user can select said open position of said valve or said closed position of said valve.

14. A collection and drainage device as recited in claim 6, wherein said capacity selector further comprises:
　a. a control valve comprised of a working spool positioned between said common inflow tube and said divided inflow tube, having a stem; and
　b. an external valve control member attached to said working spool such that said user can manipulate said working spool such that said stem blocks said flow of said bodily fluids from entering said second collection chamber.

15. A collection and drainage device as recited in claim 6, wherein said first inflow tube prong and second inflow tube prong further comprises:
　a. a first anti-reflux flap such that said first anti-reflux flap prevents said flow of said bodily fluid from flowing back into said catheter tube from said first collection chamber; and
　b. a second anti-reflux flap such that said second anti-reflux flap prevents said flow of said bodily fluid from flowing back into said catheter tube from said second collection chamber.

\* \* \* \* \*